US007708907B1

(12) United States Patent
Huang et al.

(10) Patent No.: US 7,708,907 B1
(45) Date of Patent: May 4, 2010

(54) LIQUID CRYSTAL COMPOUNDS AND LIQUID CRYSTAL COMPOSITIONS COMPRISING THE SAME

(75) Inventors: Peu-Jane Huang, Taipei (TW); An-Cheng Chen, Hsinchu (TW); Kung-Lung Cheng, Hsinchu (TW); Shih-Hsien Liu, Jhubei (TW)

(73) Assignee: Industrial Technology Research Institute, Hsinchu County (TW)

( * ) Notice: Subject to any disclaimer, the term of this patent is extended or adjusted under 35 U.S.C. 154(b) by 0 days.

(21) Appl. No.: 12/399,998

(22) Filed: Mar. 9, 2009

(30) Foreign Application Priority Data

Nov. 25, 2008 (TW) .............................. 97145463 A

(51) Int. Cl.

*C09K 19/34* (2006.01)
*C09K 19/30* (2006.01)
*C09K 19/12* (2006.01)
*C09K 19/20* (2006.01)
*C07D 241/04* (2006.01)
*C07D 241/52* (2006.01)

(52) U.S. Cl. ............................ 252/299.61; 252/299.63; 252/299.66; 252/299.67; 544/358; 544/383; 544/392; 544/398; 544/403

(58) Field of Classification Search ................. 544/358, 544/383, 392, 398, 403; 252/299.61, 299.63, 252/299.66, 299.67

See application file for complete search history.

(56) References Cited

U.S. PATENT DOCUMENTS

| | | | | |
|---|---|---|---|---|
| 6,495,066 | B1 | 12/2002 | Wu | |
| 7,622,056 | B2 * | 11/2009 | Cheng et al. | 252/299.61 |
| 2008/0135803 | A1 * | 6/2008 | Cheng et al. | 252/299.61 |

FOREIGN PATENT DOCUMENTS

| | | | |
|---|---|---|---|
| DE | 4234627 | A1 | 4/1994 |
| JP | 2002-14859 | A | 5/2002 |

* cited by examiner

*Primary Examiner*—Shean C Wu
(74) *Attorney, Agent, or Firm*—Pai Patent & Trademark Law Firm; Chao-Chang David Pai

(57) ABSTRACT

A liquid crystal compound of Formula (I) is provided.

(I)

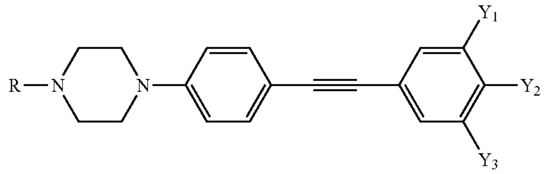

In Formula (I), $Y_1$, $Y_2$ and $Y_3$ are, independently, hydrogen, halogen, cyano or thiocyano, and R is C1-12 alkyl or C1-12 alkoxy, preferably C3-6 alkyl. The liquid crystal compound is colorless. The invention also provides a liquid crystal composition including the liquid crystal compound.

13 Claims, No Drawings

LIQUID CRYSTAL COMPOUNDS AND LIQUID CRYSTAL COMPOSITIONS COMPRISING THE SAME

CROSS REFERENCE TO RELATED APPLICATIONS

This Application claims priority of Taiwan Patent Application No. 97145463, filed on Nov. 25, 2008, the entirety of which is incorporated by reference herein.

BACKGROUND OF THE INVENTION

1. Field of the Invention

The invention relates to a liquid crystal compound, and more particularly to a liquid crystal compound containing piperazine.

2. Description of the Related Art

Liquid crystals possess dielectric and optical anisotropy, superior molecule alignment and fluidity. When stimulated by light, heat, of an electric field or magnetic field, molecule alignments of liquid crystals are easily altered to form contrast or specific optical effects. A display fabricated thereby possesses a light weight, portability, fine size and low power consumption. Thus, recently, liquid crystals have become a popular display medium for various portable electric and information products, such as digital watches, calculator and automotive instrument panels, twisted nematic (TN) LCDs, super twisted nematic (STN) LCDs, notebook computers, optical grating of components of projectors and memory cells of printers.

An ideal liquid crystal material possesses superior chemical properties, for example, a wide nematic liquid crystal phase, a low melting point, low fusion heat, physicochemical stability and achromatization, and simultaneously possess superior physical properties, for example, high dielectric anisotropy ($\Delta\in$) and high birefringence ($\Delta n$) properties.

BRIEF SUMMARY OF THE INVENTION

One embodiment of the invention provides a liquid crystal compound of Formula (I):

(I)

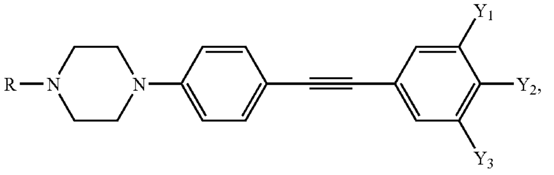

wherein $Y_1$, $Y_2$ and $Y_3$ are, independently, hydrogen, halogen, cyano or thiocyano, and R is C1-12 alkyl or C1-12 alkoxy.

One embodiment of the invention provides a liquid crystal composition comprising a first liquid crystal compound of Formula (I) and a second liquid crystal compound of Formulas (Z1)-(Z9):

(I)

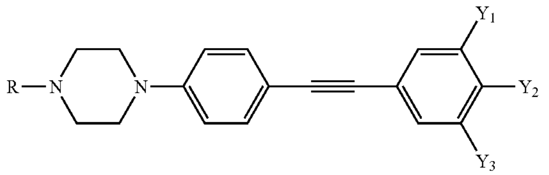

(Z1)

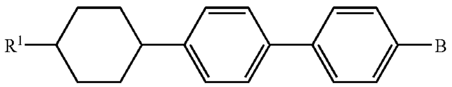

(Z2)

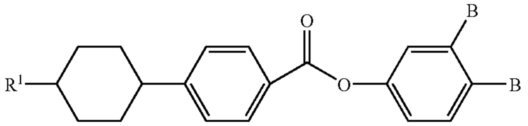

(Z3)

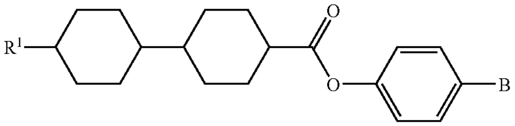

(Z4)

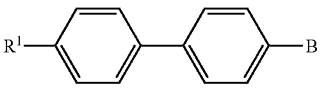

(Z5)

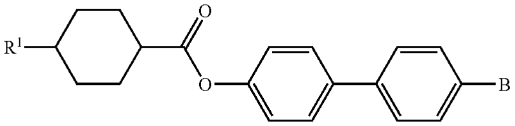

(Z6)

$$R^2—A1—Z^1—A2—R^3$$

(Z7)

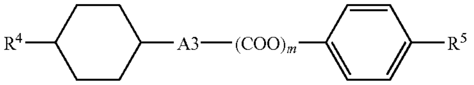

(Z8)

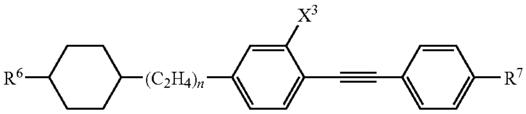

and (Z9)

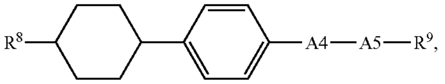

wherein $R^1$ is C1-9 alkyl, B is halogen or cyano, and $R^2$, $R^3$ and $R^4$ are, independently, C1-10 alkyl, wherein methylene is replaced by oxygen or ethylenyl and at least one hydrogen is replaced by fluorine, and $R^5$ and $R^8$ are, independently, C1-10 alkyl, wherein methylene is replaced by oxygen, and $R^6$, $R^7$ and $R^9$ are, independently, C1-10 alkyl, A1, A2, A3 and A5 are, independently, trans-1,4-cyclohexylene or 1,4-phenylene, and A4 is 1,4-phenylene, wherein at least one hydrogen is replaced by fluorine, $Z^1$ is ethylenyl or acetylenyl, m and n are 0-2, and $X^3$ is hydrogen or fluorine, wherein the first liquid crystal compound and the second liquid crystal compound have a weight ratio of 0.5:99.5-35:65.

Note that the chemical and photoelectric properties of the modified liquid crystal molecule of the invention are improved, thus facilitating application in various liquid crystal devices. Additionally, the dipole moment of the liquid crystal compound with a piperazine structure having rich electron pairs to induce resonance is increased. Meanwhile, the dielectric anisotropy (Δ∈) thereof is increased by production of an electron withdrawing effect of the polar functional groups ($Y_1$, $Y_2$ and $Y_3$). The birefringence (Δn) thereof is increased by conduction into a benzene or triple bond to extend the conjugated structure length of the main chain. Additionally, performance of a display cannot be interfered with due to conduction into the colorless polar functional groups ($Y_1$, $Y_2$ and $Y_3$), for example, halogen, cyano or thiocyano. When the liquid crystal composition with large dipole moment, low viscosity and high dielectric anisotropy is applied in TN LCDs, cholesterol LCDs or polymer dispersed LCDs, the driving voltage thereof is reduced. In addition to high dielectric anisotropy and high birefringence, the colorless liquid crystal compound possesses high thermal stability and high compatibility.

A detailed description is given in the following embodiments.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides a liquid crystal compound of Formula (I):

(I)

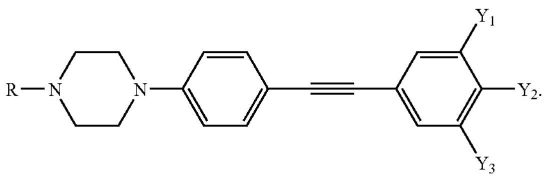

In Formula (I), $Y_1$, $Y_2$ and $Y_3$ are, independently, hydrogen, halogen, cyano or thiocyano. R is C1-12 alkyl, C1-12 alkoxy or C3-6 alkyl.

Specifically, the liquid crystal compound is colorless.

Specific liquid crystal compounds, for example, Formulas (I-1)-(1-3) are disclosed in other embodiments:

(I-1)

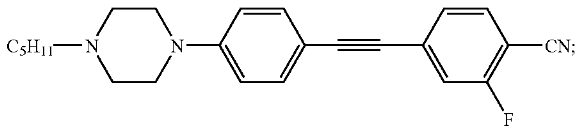

(I-2)

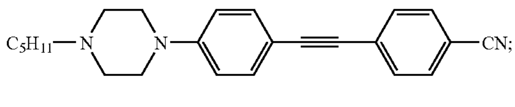

and

-continued (I-3)

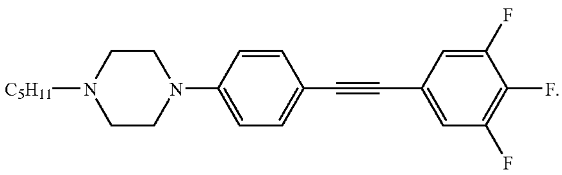

The dielectric anisotropy (Δ∈) of the liquid crystal compound is about 18-35. The birefringence (Δn) thereof is about 0.25-0.40. The liquid crystal compound can be widely used in, for example, reflective-type cholesterol LCDs, polymer dispersed LCDs, TN LCDs, STN LCDs, TFT LCDs or IPS LCDs.

Note that the chemical and photoelectric properties of the modified liquid crystal molecule of the invention are improved, thus facilitating application in various liquid crystal devices. Additionally, the dipole moment of the liquid crystal compound with a piperazine structure having rich electron pairs to induce resonance is increased. Meanwhile, the dielectric anisotropy (Δ∈) thereof is increased by production of an electron withdrawing effect of the polar functional groups ($Y_1$, $Y_2$ and $Y_3$). The birefringence (Δn) thereof is increased by conduction into a benzene or triple bond to extend the conjugated structure length of the main chain. Additionally, performance of a display cannot be interfered with due to conduction into the colorless polar functional groups ($Y_1$, $Y_2$ and $Y_3$), for example, halogen, cyano or thiocyano. When the liquid crystal composition with large dipole moment, low viscosity and high dielectric anisotropy is applied in TN LCDs, cholesterol LCDs or polymer dispersed LCDs, the driving voltage thereof is reduced. In addition to high dielectric anisotropy and high birefringence, the colorless liquid crystal compound possesses high thermal stability and high compatibility.

One embodiment of the invention provides a liquid crystal composition comprising a first liquid crystal compound of Formula (I) and a second liquid crystal compound of Formulas (Z1)-(Z9):

(I)

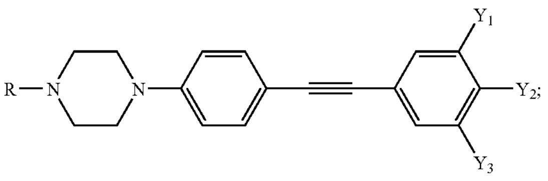

(Z1)

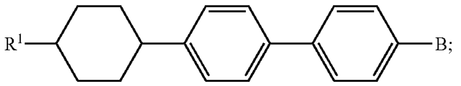

(Z2)

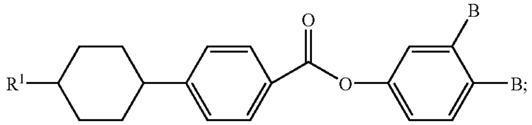

-continued (Z3)

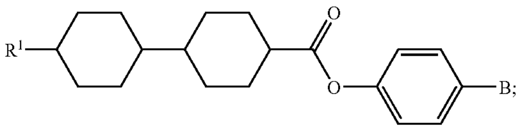

(Z4)

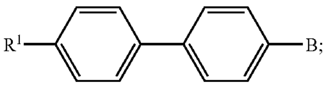

(Z5)

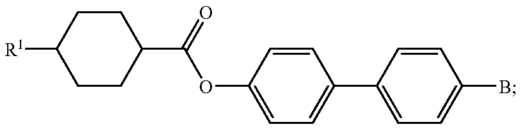

(Z6)

$R^2—A1—Z^1—A2—R^3$;

(Z7)

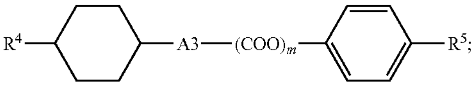

(Z8)

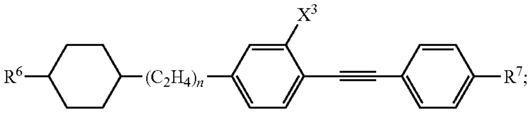

and (Z9)

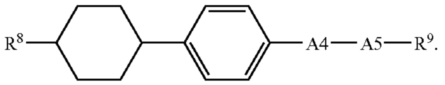

In Formulas (Z1)-(Z9), $R^1$ is C1-9 alkyl. B is halogen or cyano. $R^2$, $R^3$ and $R^4$ are, independently, C1-10 alkyl, wherein methylene is replaced by oxygen or ethylenyl and at least one hydrogen is replaced by fluorine. $R^5$ and $R^8$ are, independently, C1-10 alkyl, wherein methylene is replaced by oxygen. $R^6$, $R^7$ and $R^9$ are, independently, C1-10 alkyl. A1, A2, A3 and A5 are, independently, trans-1,4-cyclohexylene or 1,4-phenylene. A4 is 1,4-phenylene, wherein at least one hydrogen is replaced by fluorine. $Z^1$ is ethylenyl or acetylenyl. m and n are 0-2. $X^3$ is hydrogen or fluorine.

The first and second liquid crystal compounds have a weight ratio of about 0.5:99.5-35:65 or 5:95-10:90.

Example 1

Preparation of the Formula (I-1) Compound and Dielectric Anisotropy (Δ∈) and Birefringence (Δn) Thereof (I-1)

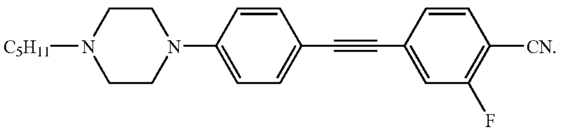

Step 1:

Synthesis Scheme:

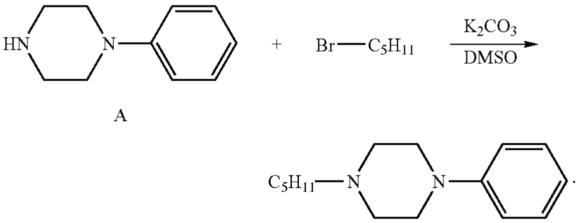

A

M1

First, under nitrogen, 1 g of compound A (6.2 mmol), 0.9 g of bromopentane (6 mmole), 1.38 g of potassium carbonate (10 mmol) and 20 mL of dimethyl sulfoxide (DMSO) were added to a reaction bottle and heated to 100-110° C. with reflux for 16 hours. After cooling, the resulting solution was repeatedly extracted with saturated salt water and ethyl acetate until DMSO was removed. After being dried by magnesium sulfate and concentrated, the crude product was purified by column chromatography. A canary yellow liquid compound M1 was obtained, with 90% of yield.

Step 2:

Synthesis Scheme:

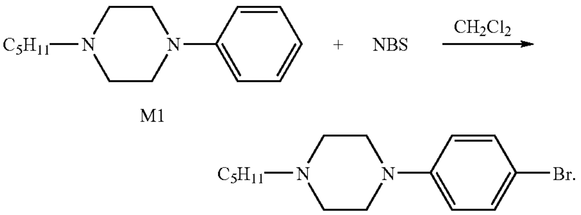

M1

M2

First, under nitrogen, 1 g of compound M1 (4.2 mmol), 1.38 g of n-bromosuccinimide (NBS) (10 mmol) and 10 mL of dichloromethane were added to a reaction bottle and allowed to react at room temperature for 16 hours. The resulting solution was then repeatedly extracted with saturated salt water and ethyl acetate. After being dried by magnesium sulfate and concentrated, the crude product was purified by column chromatography. A canary yellow liquid compound M2 was obtained, with 90% of yield.

Step 3:

Synthesis Scheme:

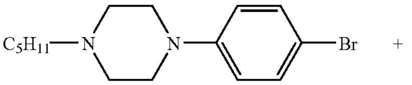

M2

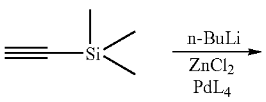

-continued

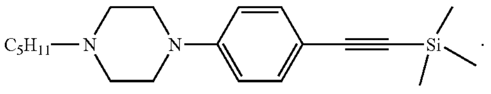

M3

First, under nitrogen, 1 g of ethynyltrimethylsilane (10.2 mmol) and 10 mL of THF were added to a reaction bottle and cooled to −78° C. using liquid nitrogen and acetone. Next, 12 mL of n-BuLi was added and allowed to react for 20 minutes. 2.4 g of zinc chloride (18.3 mmol) dissolved in THF was then added to the reaction bottle and continuously reacted for 20 minutes in the low temperature state. After warming to 0° C., 2.1 g of compound M2 (10.2 mmol) and 0.3 g of tetrakis (triphenylphosphine) palladium (0.3 mmol) dissolved in THF were added to the reaction bottle and allowed to react at 60° C. with reflux for 12 hours. The reaction was terminated by adding $NH_4Cl$. The resulting solution was then repeatedly extracted with saturated salt water and ethyl acetate. After being dried by magnesium sulfate and concentrated, the crude product was purified by column chromatography. A canary yellow solid compound M3 was obtained, with 70% of yield.

Step 4:

Synthesis Scheme:

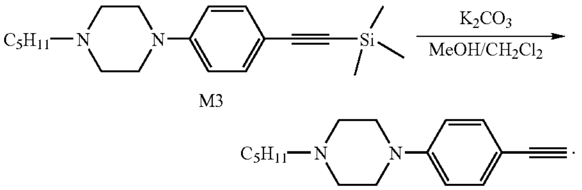

M3

M4

First, under nitrogen, 1 g of compound M3 (3 mmol), 10 mL of methanol/dichloromethane (1/1) and 0.4 g of potassium carbonate (4.5 mmol) were added to a reaction bottle and allowed to react at room temperature for 12 hours. The resulting solution was then repeatedly extracted with 20 mL of dichloromethane. After being dried by magnesium sulfate and concentrated, the crude product was purified by column chromatography. A canary yellow solid compound M4 was obtained, with 75% of yield.

Step 5:

Synthesis Scheme:

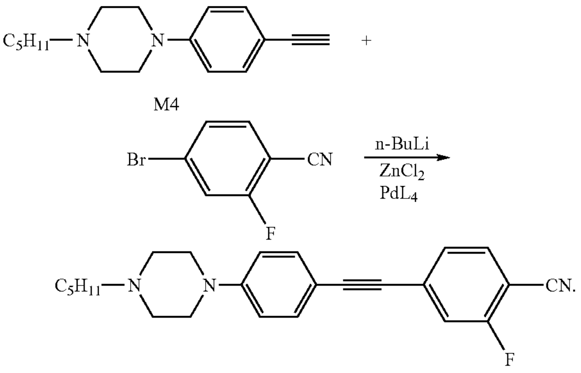

M4

I-1

First, under nitrogen, 1 g of compound M4 (3.9 mmol) and 5 mL of THF were added to a reaction bottle and cooled to −78° C. using liquid nitrogen and acetone. Next, 1.7 mL of n-BuLi was added and allowed to react for 20 minutes. 0.9 g of zinc chloride (7 mmol) dissolved in THF was then added to the reaction bottle and continuously reacted for 20 minutes in the low temperature state. After warming to 0° C., 0.8 g of 4-bromo-2-fluorobenzonitrile (3.9 mmol) and 0.2 g of tetrakis(triphenylphosphine) palladium (0.2 mmol) dissolved in THF were added to the reaction bottle and allowed to react at 60° C. with reflux for 12 hours. The reaction was terminated by adding $NH_4Cl$. The resulting solution was then repeatedly extracted with saturated salt water and ethyl acetate. After being dried by magnesium sulfate and concentrated, the crude product was purified by column chromatography. A white solid compound I-1 was obtained, with 65% of yield. The dielectric anisotropy (Δ∈) of compound I-1 was 31.8. The birefringence (Δn) thereof was 0.3763. The preparations of compound I-2 and compound I-3 were similar to that of compound I-1. The distinction thereamong was merely different reactants used in step 5. A person skilled in the art can simply prepare compound I-2 and compound I-3 according to Example 1. The dielectric anisotropy (Δ∈) of compound I-2 was 26.9. The birefringence (Δn) of compound I-2 was 0.3206. The dielectric anisotropy (Δ∈) of compound I-3 was 18.8. The birefringence (Δn) of compound I-3 was 0.2685. Comparison of the dielectric anisotropy (Δ∈) and the birefringence (Δn) between compounds I-1-I-3 and conventional liquid crystal molecules with similar structures is shown in Table 1.

TABLE 1

| | Dielectric anisotropy (Δϵ) | Birefringence (Δn) |
|---|---|---|
| Compound I-1 | 31.8 | 0.3763 |
| Compound I-2 | 26.9 | 0.3206 |
| Compound I-3 | 18.8 | 0.2685 |
| 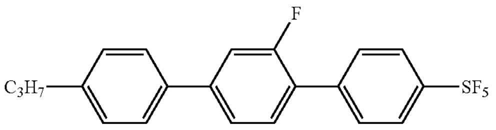 | 19.8 | 0.146 |

TABLE 1-continued

| | Dielectric anisotropy (Δϵ) | Birefringence (Δn) |
|---|---|---|
| 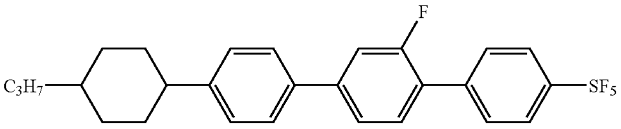 | 15.4 | 0.119 |
| 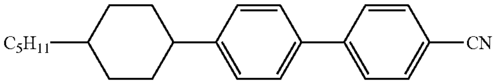 | 16.7 | 0.2 |

The results indicated that the dielectric anisotropy (Δ∈) of compounds I-1 to I-3 was higher than that of the conventional liquid crystal molecules due to conduction into a piperazine group having rich unshared electron pairs capable of inducing resonance to increase molecule dipole moment. Also, the birefringence (Δn) of compounds I-1 to I-3 was apparently higher than that of the conventional liquid crystal molecules due to conduction into a triple bond to extend the conjugated structure length of the liquid crystal molecule main chain.

Example 2

Preparation of the Liquid Crystal Composition (1) and Dielectric Anisotropy (Δ∈) and Birefringence (Δn) Thereof Compound I-1 and a liquid crystal mixture (YY066-042) were mixed with a ratio of 5:95 to form a liquid crystal composition. The liquid crystal mixture (YY066-042) comprised 8% of 5HBBCN, 24.1% of 5HBCN, 7.7% of 5HBEBFCN, 13.5% of 5HBF, 7% of 2HEBFCN, 6.5% of 3HHEBF, 3.5% of 5HHEBF, 1.7% of 2BBCN, 4.9% of 3HEBBCN, 15.4% of 5BEBFCN and 7.7% of 3HBEBFCN. The dielectric anisotropy (Δ∈) of the liquid crystal mixture (YY066-042) was 17.3. The birefringence (Δn) thereof was 0.1355. The driving voltage of the device formed by the liquid crystal mixture (YY066-042) was 1.043V. After adding compound I-1, the dielectric anisotropy (Δ∈) of the liquid crystal composition increased to 18.1. The birefringence (Δn) thereof increased to 0.1475. The driving voltage of the device formed by the liquid crystal mixture (YY066-042) and Compound I-1 was reduced to 1.023V. Note that for each component of the liquid crystal mixture (YY066-042), each code name was corresponded to various chemical formulas, for example, code name 2 represents $C_2H_5$—, code name 3 represents $C_3H_7$—, code name 5 represents $C_5H_{11}$—, code name H represents

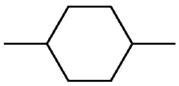, code name B represents

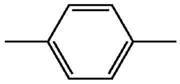, code name CN represents CN, code name E represents —COO—, and code name F represents —F.

Example 3

Preparation of the Liquid Crystal Composition (2) and Dielectric Anisotropy (Δ∈) and Birefringence (Δn) Thereof Compound I-2 and a liquid crystal mixture (DH0381-110) were mixed with a ratio of 5:95 to form a liquid crystal composition. The liquid crystal mixture (DH0381-110) comprised 10.3% of 5HBBCN, 7.2% of 3HBO2, 12.6% of 2BBCN, 31.9% of 5BBCN, 10% of 3HEBBCN, 21.8% of 7BBCN and 6.2% of 5BEBBCN. The dielectric anisotropy (Δ∈) of the liquid crystal mixture (DH0381-110) was 13.49. The birefringence (Δn) thereof was 0.0987. The driving voltage of the device formed by the liquid crystal mixture (DH0381-110) was 1.862V. After adding compound I-2, the dielectric anisotropy (Δ∈) of the liquid crystal composition increased to 14.27. The birefringence (Δn) thereof increased to 0.1112. The driving voltage of the device formed by the liquid crystal mixture (DH0381-110) and Compound I-2 was reduced to 1.434V. Note that for each component of the liquid crystal mixture (DH0381-110), each code name was corresponded to various chemical formulas, for example, code name 2 represents $C_2H_5$—, code name 3 represents $C_3H_7$—, code name 5 represents $C_5H_{11}$—, code name 7 represents $C_7H_{15}$—, code name H represents

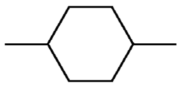, code name B represents

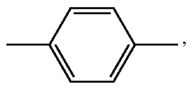

code name CN represents CN, code name F represents F, code name 0 represents —O—, and code name E represents —COO—.

Example 4

Preparation of the Liquid Crystal Composition (3) and Dielectric Anisotropy (Δ∈) and Birefringence (Δn) Thereof Compound I-3 and a liquid crystal mixture (LOT3) were mixed with a ratio of 10:90 to form a liquid crystal composition. The liquid crystal mixture (LOT3) comprised 2.5% of 5HBF, 2.5% of 6HBF, 2.5% of 7HBF, 9.6% of 3HHB(F)F, 2.5% of 3HBEB(FF)F, 2% of 4HBEB(FF)F, 6.2% of 3HHEB (FF)F, 4.9% of 3HHB(FF)F, 9.6% of 3HBB(FF)F, 9.7% of 5HBB(FF)F, 5.2% of 4HHB(FF)F, 4.5% of 5HHB(FF)F, 9.9% of 3HHV, 4.7% of 3HBB(F)F, 9.8% of 3HH2B(F)F, 9.1% 1BHHV and 4.8% of 2BB(F)B3. The dielectric anisotropy (Δ∈) of the liquid crystal mixture (LOT3) was 7.38. The birefringence (Δn) thereof was 0.0987. The driving voltage of the device formed by the liquid crystal mixture (LOT3) was 1.862V. After adding compound I-3, the dielectric anisotropy (Δ∈) of the liquid crystal composition increased to 8.545. The birefringence (Δn) thereof increased to 0.1158. The driving voltage of the device formed by the liquid crystal mixture (LOT3) and Compound I-3 was reduced to 1.802V. Note that for each component of the liquid crystal mixture (LOT3), each code name was corresponded to various chemical formulas, for example, code name 1 represents $CH_3$—, code name 3 represents $C_3H_7$—, code name 4 represents $C_4H_9$—, code name 5 represents $C_5H_{11}$—, code name 6 represents $C_6H_{13}$—, code name 7 represents $C_7H_{15}$—, code name H represents

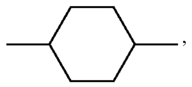

code name B represents

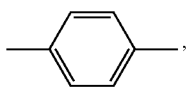

code name B(F) represents

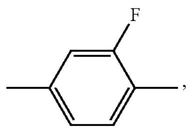

code name B(FF) represents

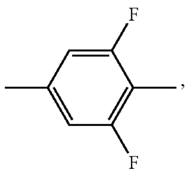

code name F represents F, code name E represents —COO—, and code name V represents $CH_2$═CH—.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A liquid crystal compound of Formula (I):

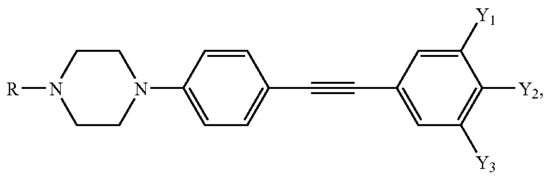

wherein $Y_1$, $Y_2$ and $Y_3$ are, independently, hydrogen, halogen, cyano or thiocyano; and R is C1-12 alkyl or C1-12 alkoxy.

2. The liquid crystal compound as claimed in claim 1, wherein R is C3-6 alkyl.

3. The liquid crystal compound as claimed in claim 1, wherein $Y_1$ is fluorine, $Y_2$ is cyano and $Y_3$ is fluorine.

4. The liquid crystal compound as claimed in claim 3, wherein R is C3-6 alkyl.

5. The liquid crystal compound as claimed in claim 1, wherein $Y_1$ is hydrogen, $Y_2$ is cyano and $Y_3$ is fluorine.

6. The liquid crystal compound as claimed in claim 5, wherein R is C3-6 alkyl.

7. The liquid crystal compound as claimed in claim 1, wherein $Y_1$ is hydrogen, $Y_2$ is cyano and $Y_3$ is hydrogen.

8. The liquid crystal compound as claimed in claim 7, wherein R is C3-6 alkyl.

9. The liquid crystal compound as claimed in claim 1, wherein $Y_1$ is fluorine, $Y_2$ is fluorine and $Y_3$ is fluorine.

10. The liquid crystal compound as claimed in claim 9, wherein R is C3-6 alkyl.

11. The liquid crystal compound as claimed in claim 1, wherein the liquid crystal compound is colorless.

12. A liquid crystal composition, comprising:

a first liquid crystal compound of Formula (I) as claimed in claim 1; and a second liquid crystal compound of Formulas (Z1)-(Z9):

(Z1)

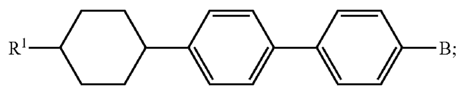

-continued (Z2)

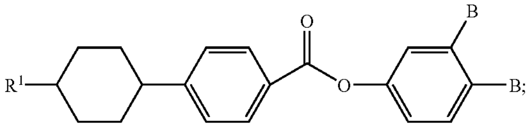

(Z3)

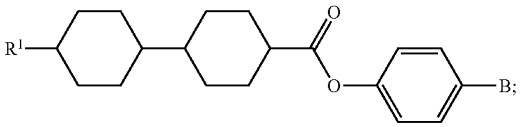

(Z4)

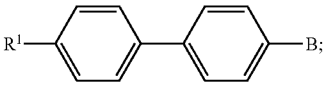

(Z5)

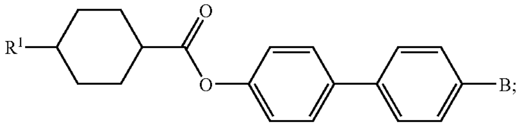

(Z6)

$R^2$—A1—$Z^1$—A2—$R^3$;

(Z7)

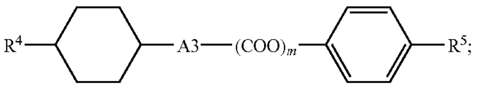

(Z8)

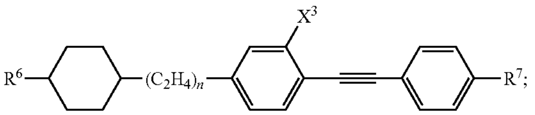 and

-continued (Z9)

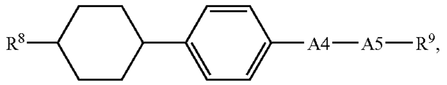

wherein $R^1$ is C1-9 alkyl;

B is halogen or cyano;

$R^2$, $R^3$ and $R^4$ are independently C1-10 alkyl, wherein methylene is optionally replaced by oxygen or ethylenyl and at least one hydrogen atom is optionally replaced by fluorine;

$R^5$ and $R^8$ are independently C1-10 alkyl, wherein methylene is optionally replaced by oxygen;

$R^6$, $R^7$ and $R^9$ are independently C1-10 alkyl;

A1, A2, A3 and A5 are independently trans-1,4-cyclohexylene or 1,4-phenylene;

A4 is 1,4-phenylene, wherein at least one hydrogen is optionally replaced by fluorine;

$Z^1$ is ethylenyl or acetylenyl;

m and n are 0-2;

$X^3$ is hydrogen or fluorine; and wherein the first and second liquid crystal compounds have a weight ratio of about 0.5:99.5-35:65.

13. The liquid crystal composition as claimed in claim 12, wherein the first liquid crystal compound and the second liquid crystal compound have a weight ratio of 5:95-10:90.

* * * * *